US005756496A

United States Patent [19]
Ham et al.

[11] Patent Number: 5,756,496
[45] Date of Patent: May 26, 1998

[54] AMIDE DERIVATIVES HAVING 5HT1D-ANTAGONIST ACTIVITY

[75] Inventors: Peter Ham, Harlow; Laramie Mary Gaster, Bishops Stortford; David Francis King, Bishops Stortford; David Malcolm Duckworth, Bishops Stortford, all of United Kingdom

[73] Assignee: SmithKline Beecham p.l.c., Brentford, England

[21] Appl. No.: 737,660

[22] PCT Filed: May 16, 1995

[86] PCT No.: PCT/EP95/01890

§ 371 Date: Nov. 21, 1996

§ 102(e) Date: Nov. 21, 1996

[87] PCT Pub. No.: WO95/32967

PCT Pub. Date: Dec. 7, 1995

[30] Foreign Application Priority Data

May 28, 1994 [GB] United Kingdom ............... 9410780
May 28, 1994 [GB] United Kingdom ............... 9410781

[51] Int. Cl.[6] ........................ C07D 413/12; A01K 31/55
[52] U.S. Cl. ............... 514/211; 514/233.8; 514/364; 540/552; 544/105; 548/131
[58] Field of Search ........................ 548/131; 540/552; 544/105; 514/364, 233.8, 211

[56] References Cited

FOREIGN PATENT DOCUMENTS

| 0533266 | 3/1993 | European Pat. Off. |
| 0533267 | 3/1993 | European Pat. Off. |
| 0533268 | 3/1993 | European Pat. Off. |

OTHER PUBLICATIONS

P.H. Hutson et al., "The effects of GR127935, a putative 5-HT1D receptor antagonist, on brain 5-HT metabolism, extracellular 5-HT concentration and behavior in the guinea pig", Neuropharmacology, 34(4), pp. 383–392 (1995).

M. Skingle et al., "Effects of the 5-HT1D receptor antagonist GR127935 on extracellular levels of 5-HT in the guinea pig frontal cortex as measured by microdialysis", Neuropharmacology, 34(4), pp. 377–382 (1995).

Primary Examiner—Robert Gerstl
Attorney, Agent, or Firm—Wayne J. Dustman; Charles M. Kinzig; Edward T. Lentz

[57] ABSTRACT

Compound of formula (1), processes for their preparation and their use as CNS agents are disclosed, in which A is CONR where R is hydrogen or $C_{1-6}$alkyl; Q is an optionally substituted 5 to 7-membered heterocyclic ring containing 1 to 3 heteroatoms selected from oxygen, nitrogen or sulphur, $R^1$ is hydrogen, halogen, $C_{1-6}$alkyl, $C_{3-6}$cycloalkyl, $COC_{1-6}$-alkyl, $C_{1-6}$alkoxy, hydroxy, hydroxy$C_{1-6}$alkyl, hydroxy$C_{1-6}$alkoxy, $C_{1-6}$alkoxy$C_{1-6}$alkoxy, acyl, nitro, trifluoromethyl, cyano, $SR^9$, $SOR^9$, $SO_2R^9$, $SO_2NR^{10}R^{11}$, $CO_2R^{10}$, $CONR^{10}R^{11}$, $CO_2NR^{10}R^{11}$, $CONR^{10}(CH_2)_aCO_2R^{11}$, $(CH_2)_aNR^{10}R^{11}$, $(CH_2)_aCONR^{10}R^{11}$, $(CH_2)_aNR^{10}COR^{11}$, $(CH_2)_aCO_2C_{1-6}$alkyl, $CO_2(CH_2)_aOR^{10}$, $NR^{10}R^{11}$, $NR^{10}CO_{2/R}{}^{11}$, $NR^{10}CONR^{10}R^{11}$, $CR^{10}=NOR^{11}$, $CNR^{10}=NOR^{11}$, where $R^{10}$ and $R^{11}$ are independently hydrogen or $C_{1-6}$alkyl and a is 1 to 4 or $R^1$ is an optionally substituted 5 to 7-membered heterocyclic ring containing 1 to 3 heteroatoms selected from oxygen, nitrogen or sulphur, $R^2$ and $R^3$ are independently hydrogen, halogen, $C_{1-6}$alkyl, $C_{3-6}$cycloallyl, $C_{3-6}$cycloalkenyl, $C_{1-6}$alkoxy, acyl, aryl, acyloxy, hydroxy, nitro, trifluoromethyl, cyano, $CO_2R^{10}$, $CONR^{10}R^{11}$, $NR^{10}R^{11}$ where $R^{10}$ and $R^{11}$ are as defined for $R^1$; $R^4$ and $R^5$ are independently hydrogen or $C_{1-6}$alkyl; $R^6$ is halogen, hydroxy, $C_{1-6}$alkyl or $C_{1-6}$alkoxy; $R^7$ and $R^8$ are independently hydrogen, $C_{1-6}$alkyl, aralkyl, or together with the nitrogen atom to which they are attached form an optionally substituted 5 to 7-membered heterocyclic ring containing one or two heteroatoms selected from oxygen, nitrogen or sulphur, m is 0 to 4; and n is 0, 1 or 2.

10 Claims, No Drawings

AMIDE DERIVATIVES HAVING 5HT1D-ANTAGONIST ACTIVITY

The present invention relates to novel amide derivatives, processes for their preparation, and pharmaceutical compositions containing them.

EPA 0 533 266 17/8 disclose a series of benzanilide derivatives which are said to possess $^5$HT1D receptor antagonist activity. These compounds are said to be of use in the treatment of various CNS disorders.

A structurally distinct class of compounds have now been discovered and have been found to exhibit $5HT_{1D}$ antagonist activity. In a first aspect, the present invention therefore provides a compound of formula (1) or a salt thereof:

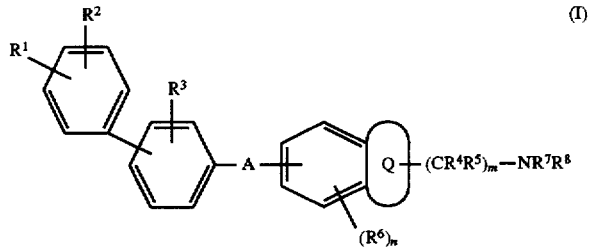

in which A is CONR where R is hydrogen or $C_{1-6}$alkyl; Q is an optionally substituted 5 to 7-membered heterocyclic ring containing 1 to 3 heteroatoms selected from oxygen, nitrogen or sulphur; $R^1$ is hydrogen, halogen, $C_{1-6}$alkyl, $C_{3-6}$cycloalkyl, $COC_{1-6}$alkyl, $C_{1-6}$alkoxy, hydroxy, hydroxy$C_{1-6}$alkyl, hydroxy$C_{1-6}$aLkoxy$C_{1-6}$alkoxy, acyl, nitro, trifluoromethyl, cyano, $SR^9$, $SOR^9$, $SO_2R^9$, $SO_2NR^{10}R^{11}$, $CO_2R^{10}$, $CONR^{10}R^{11}$, $CO_2NR^{10}R^{11}$, $CONR^{10}(CH_2)_aCO_2R_{11}$, $(CH_2)_aNR^{10}R^{11}$, $(CH_2)_aCONR^{10}R^{11}$, $(CH_2)_aNR^{10}COR^{11}$, $(CH_2)_aCO_2C_{1-6}$alkyl, $CO_2(CH_2)_aOR^{10}$, $NR^{10}R^{11}$, $NR^{10}CO_2R^{11}$, $NR^{11}CONR^{10}R^{11}$, $CR^{10}=NOR^{11}$, $CNR^{10}=NOR^{11}$, where $R^{10}$ and $R^{11}$ are independently hydrogen or $C_{1-6}$alkyl and a is 1 to 4 or $R^1$ is an optionally substituted 5 to 7-membered heterocyclic ring containing 1 to 3 heteroatoms selected from oxygen, nitrogen or sulphur; $R^2$ and $R^3$ are independently hydrogen, halogen, $C_{1-6}$alkyl, $C_{3-6}$cycloallyl, $C_{3-6}$cycloalkenyl, $C_{1-6}$alkoxy, acyl, aryl, acyloxy, hydroxy, nitro, trifluoromethyl, cyano, $CO_2R^{10}$, $CONR^{10}R^{11}$, $NR^{10}R^{11}$ where $R^{10}$ and $R^{11}$ are as defined for $R^1$; $R^4$ and $R^5$ are independently hydrogen or $C_{1-6}$alkyl; $R^6$ is halogen, hydroxy, $C_{1-6}$alkyl or $C_{1-6}$alkoxy; $R^7$ and $R^8$ are independently hydrogen, $C_{1-6}$alkyl, aralkyl, or together with the nitrogen atom to which they are attached form an optionally substituted 5- to 7-membered heterocyclic ring containing one or two heteroatoms selected from oxygen, nitrogen or sulphur; m is 0 to 4; and n is 0, 1 or 2.

$C_{1-6}$alkyl groups, whether alone or as part of another group, may be straight chain or branched.

Suitably $R^1$ is hydrogen, halogen, $C_{1-6}$alkyl, $C_{3-6}$cycloalkyl, $COC_{1-6}$alkyl, $C_{1-6}$alkoxy, hydroxy, hydroxy$C_{1-6}$alkyl, hydroxy$C_{1-6}$alkoxy, $C_{1-6}$alkoxy$C_{1-6}$alkoxy, acyl, nitro, trifluoromethyl, cyano, $SR^9$, $SOR^9$, $SO_2R^9$, $SO_2NR^{10}R^{11}$, $CO_{hd 2}R^{10}$, $CONR^{10}R^{11}$, $CO_2NR^{10}R^{11}$, $CONR^{10}(CH_2)_aCO_2R^{11}$, $(CH_2)_aNR^{10}R^{11}$, $(CH_2)_aCONR^{10}R^{11}$, $(CH_2)_aNR^{10}COR^{11}$, $(CH_2)_aCO_2C_{1-6}$alkyl, $CO_2(CH_2)_aOR^{10}$, $NR^{10}R^{11}$, $NR^{10}CO_2R^{11}$, $NR^{10}CONR^{10}R^{11}$, $CR^{10}=NOR^{11}$, $CNR^{10}=NOR^{11}$, where $R^{10}$ and $R^{11}$ are independently hydrogen or $C_{1-6}$alkyl and a is 1 to 4 or $R^1$ is an optionally substituted 5 to 7-membered heterocyclic ring containing 1 to 3 heteroatoms selected from oxygen, nitrogen or sulphur;

When $R^1$ is a 5 to 7-membered heterocyclic ring containing 1 to 3 heteroatoms selected from oxygen, nitrogen or sulphur suitable heterocyclic rings include thienyl, furyl, pyrrolyl, triazolyl, diazolyl, imidazolyl, oxadiazolyl, isothiazolyl, isoxazolyl, thiadiazolyl, pyridyl, pyrimidyl and pyrazinyl. The heterocyclic rings can be linked to the remainder of the molecule via a carbon atom or, when present, a nitrogen atom. Suitable substituents for these rings include $R^2$ and $R^3$ groups as defined above. Preferably $R^1$ is oxadiazolyl, most preferably a 5-methyl-1,2,4-oxadiazol-3-yl group.

Suitably $R^2$ and $R^3$ are independently hydrogen, halogen, $C_{1-6}$alkyl, $C_{3-6}$cycloalkyl, $C_{3-6}$cycloalkenyl, $C_{1-6}$alkoxy, acyl, aryl, acyloxy, hydroxy, nitro, trifluoromethyl, cyano, $CO_2R^{10}$, $CONR^{10}R^{11}$, $NR^{10}R^{11}$ where $R^{10}$ and $R^{11}$ are as defined for $R^1$. Preferably $R^2$ is $C_{1-6}$alkyl, in particular methyl. Preferably $R^3$ is hydrogen.

Suitably A is CONR where R is hydrogen or $C_{1-6}$alkyl. Preferably A is CONH.

Suitably Q is an optionally substituted 5 to 7-membered heterocyclic ring containing 1 to 3 heteroatoms selected from oxygen, nitrogen or sulphur. Preferably Q is a 5- or 6-membered ring containing one or two heteroatoms. Preferably Q, together with the phenyl group to which it it attached, forms an indole, indoline, benzoxazole, benzopyran or benzoxazine ring. Suitable optional substituents for the ring Q include groups $R^1$ and $R^2$ as defined above. Preferred substituents include $C_{1-6}$ alkyl, particularly methyl, and carbonyl groups.

Suitably $R^4$ and $R^5$ are independently hydrogen or $C_{1-6}$alkyl. Preferably $R^4$ and $R^5$ are both hydrogen.

The group —$(CR^4R^5)_m NR^7R^8$ can be attached to the ring Q at any suitable position, and can be attached to a carbon atom or, when present, a nitrogen atom.

Suitably $R^7$ and $R^8$ are independently hydrogen, $C_{1-6}$alkyl, aralkyl, or together with the nitrogen atom to which they are attached form an optionally substituted 5-to 7-membered heterocyclic ring containing one or two heteroatoms selected from oxygen, nitrogen or sulphur. Examples of $R^7$ and $R^8$ as heterocyclic rings include pyrrolidine, morpholine, piperazine and piperidine. Optional substituents for such rings include $C_{1-6}$alkyl. Preferably $R^7$ and $R^8$ are both $C_{1-6}$alkyl, in particular methyl.

Suitably $R^6$ is halogen, hydroxy, $C_{1-6}$alkyl or $C_{1-6}$alkoxy.

Suitably m is 0 to 4, preferably m is 2.

Suitably n is 0, 1 or 2, preferably n is 0.

The groups $R^1$, $R^2$ and $R^3$ can be attached to their respective rings at any suitable position.

Particularly preferred compounds of the invention include: N-[1-(2-Dimethylaminoethyl)-1H-indol-6-yl]-2'-methyl-4'-(5-methyl-1,2,4-oxadiazol-3-yl)biphenyl-4-carboxamide, N-[2,3-Dihydro-1-(2-dimethylaminoethyl)-1H-indol-6-yl]-2'-methyl-4'-(5-methyl-1,2,4-oxadiazol-3-yl) biphenyl-4-carboxamide, N-[4-(2-Dimethylaminoethyl)-3,4-dihydro-2H- 1,4-benzoxazin-6-yl]-2'-methyl-4'-(5-methyl-1,2,4-oxadiazol-3-yl)biphenyl-4-carboxamide, N-[3-(2-Dimethylaminoethyl)-1H-indol-5-yl]-2'-methyl-4'-(5-methyl-1,2,4-oxadiazol-3-yl)biphenyl-4-carboxamide, N-[4-(2-Dimethylaminoethyl)-3,4-dihydro-3-oxo-2H-1,4-benzoxazin-6-yl]-2'-methyl-4'-(5-methyl-1,2,4-oxadiazol-3-yl)biphenyl-4-carboxamide, N-[4-(2-Dimethylaminoethyl)-3,4-dihydro-3-methyl-2H-1,4-benzoxazin-6-yl]-2'-methyl-4'-(5-methyl-1,2,4-oxadiazol-3-yl)biphenyl-4-carboxamide, N-[4-(2-Dimethylaminoethyl)-3,4-dihydro-2H-benzo[b] pyran-6-yl]-2'-methyl-4'-(5-methyl-1,2,4-oxadiazol-3-yl) biphenyl-4-carboxamide, N-[3-(2-Dimethylaminoethyl)-2-oxo-2(3H)-benzoxazol-5-yl]-2'-methyl-4'-(5-methyl-1,2,4-oxadiazol-3-yl)biphenyl-4-carboxamide, N-[5-(2-Dimethylaminoethyl)-2,3,4,5-tetrahydro-1,5-benzoxazepin-7-yl]-2'-methyl-4'-(5-methyl-1,2,4-oxadiazol-3-yl) biphenyl-4-carboxamide, and pharmaceutically acceptable salts thereof.

Preferred salts of the compounds of formula (I) are pharmaceutically acceptable salts. These include acid addition salts such as hydrochlorides, hydrobromides, phosphates, acetates, fumarates, maleates, tartrates, citrates, oxalates, methanesulphonates and p-toluenesulphonates.

Certain compounds of formula (I) are capable of existing in stereoisomeric forms. It will be understood that the invention encompasses all geometric and optical isomers of the compounds of formula (I) and the mixtures thereof including racemates. Tautomers of compounds of formula (I) and mixtures thereof also form an aspect of the invention.

In a further aspect the present invention provides a process for the preparation of a compound of formula (I) which comprises.

(a) reaction of a compound of formula (II):

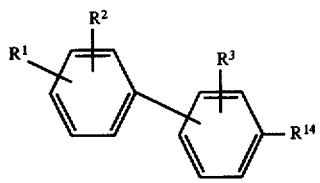

with a compound of formula (III):

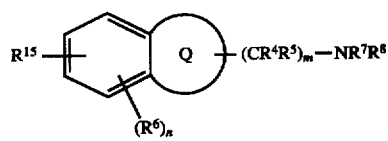

in which Q, m, $R^1$, $R^2$, $R^3$, $R^4$, $R^5$, $R^6$, $R^7$, $R^8$ and n are as defined in formula (I) and $R^{14}$ and $R^{15}$ contain the appropriate functional group(s) necessary to form the A moiety; and optionally thereafter in any order:

converting a compound of formula (I) into another compound of formula (1)

forming a pharmaceutically acceptable salt.

Suitably $R^{14}$ is an activated carboxylic acid derivative, such as an acyl halide or acid anhydride, and $R^{15}$ is an amine group. Activated compounds of formulae (II) or (III) can also be prepared by reaction of the corresponding carboxylic acid with a coupling reagent such as carbonyldiimidazole, dicyclohexylcarbodiimide or diphenylphosphorylazole. Preferably $R^{14}$ is a group COL where L is halo, particularly chloro.

A compound of formulae (II) and (III) are typically reacted together in an inert organic solvent such as DMF, TBF or dichloromethane at ambient or elevated temperature in the presence of a base such as an alkali metal hydroxide, triethylamine or pyridine.

Intermediate compounds of formulae (II) and (Im) are commercially available or can be prepared using standard procedures such as those outlined in EPA 533266n/8. Certain intermediate compounds of formulae (II) and (III) are novel and form a further aspect of the invention.

It will be appreciated to those skilled in the art that it may be necessary to protect certain reactive substituents during some of the above procedures. Standard protection and deprotection techniques can be used. For example, primary amines can be protected as phthalimide, benzyl, benzyloxycarbonyl or trityl derivatives. These groups can be removed by conventional procedures well known in the art.

Carboxylic acid groups can be protected as esters. Aldehyde or ketone groups can be protected as acetals, ketals, thioacetals or thioketals. Deprotection is achieved using standard conditions.

Certain compounds of formula (I) can be converted into further compounds of formula (I) using standard procedures.

$5HT_{1D}$ Antagonists, and in particular the compounds of the present invention, are expected to be of use in the treatment of CNS disorders such as mood disorders, including depression, seasonal effective disorder and dysthymia; anxiety disorders, including generalised anxiety, panic disorder, agoraphobia, social phobia, obsessive compulsive disorder and post-traumatic stress disorder; memory disorders, including dementia, amnestic disorders and age-associated memory impairment; and disorders of eating behaviours, including anorexia nervosa and bulimia nervosa. Other CNS disorders include Parkinson's disease, dementia in Parkinson's disease, neuroleptic-induced Parkinsonism and tardive dyskinesias, as well as other psychiatric disorders.

5HT1D Antagonists, and in particular compounds of the present invention, may also be of use in the treatment of endocrine disorders such as hyperprolactinaemia, in the treatment of vasospasm (particularly in the cerebral vasculature) and hypertension, as well as disorders in the gastrointestinal tract where changes in motility and secretion are involved. They may also be of use in the treatment of sexual dysfunction.

Therefore, the present invention, provides a compound of general formula (I) or a physiologically acceptable salt or solvate thereof for use in therapy.

The present invention also provides a compound of general formula (I) or a physiologically acceptable salt or solvate thereof for use in the treatment of the aforementioned disorders.

In another aspect the invention provides the use of a compound of general formula (I) or a pharmaceutically acceptable salt or solvate thereof for the manufacture of a medicament for the treatment of the aforementioned disorders.

In a further aspect the invention provides a method of treating the aforementioned disorders which comprises administering an effective amount to a patient in need of such treatment of a compound of general formula (I) or a pharmaceutically acceptable salt or solvate thereof.

In particular the invention provides a compound of general formula (I) or a physiologically acceptable salt or solvate thereof for use in the treatment or prophylaxis of depression.

It will be appreciated by those skilled in the art that the compounds according to the invention may advantageously be used in conjunction with one or more other therapeutic agents, for instance, different antidepressant agents.

The present invention also provides a pharmaceutical composition, which comprises a compound of formula (1) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

The following examples illustrate the preparation of compounds of the invention.

Description 1 1-(2-Dimethylaminoethyl)-6-nitro-1H-indole

A solution of 2-dimethylaminoethyl chloride (0.86 g, 8 mmol) in dry toluene (30 ml) was added to a mixture of 6-nitroindole (0.63 g, 3.9 mmol) and potassium t-butoxide (0.44 g, 4 mmol) in dry ThF (40 ml) under an argon atmosphere. The reaction mixture was stirred at room temperature for 19 hr, then heated under reflux for 3 hr. After cooling the mixture was treated with 10% aqueous $Na_2CO_3$ solution and extracted with EtOAc. The combined organic layers were dried ($Na_2SO_4$) and evaporated under reduced pressure to give the title compound (0.89g, 98%).

$^1$H NMR (250MHz, $CDCl_3$) δ:8.31 (s, 1H), 7.97 (dd, 1H), 7.59 (d, 1H), 7.44 (d, 1H) 6.57 (d, 1H), 4.23 (t, 2H), 2.68 (t, 2H), 2.29 (s, 6H).

Description 2 6-Amino-1-(2-dimethylaminoethyl)-1H-indole

A suspension of the product from description 1 (0.14 g, 0.6 mmol) in EtOH (25 ml) was hydrogenated over 10% palladium on charcoal until hydrogen uptake ceased. The catalyst was removed by filtration through kieselguhr and the filtrate concentrated under reduced pressure to give the title compound as a brown oil. (0.14g, 100%).

$^1$H NMR (200MHz, $CDCl_3$) δ: 7.3 (d, 1H), 6.81 (s, 1H), 6.52-6.41 (m, 2H), 6.28 (s, 1H), 4.0 (t, 2H), 3.41 (brs, 2H), 2.57 (t, 2H) 2.21 (s, 6H)

Description 3 2,3-Dihydro-1-(2-dimethylaminoethyl)-6-nitro-1H-indole

The product from description 1 (0.5g 2.0mmol) was dissolved in TFA (10 ml) and the solution cooled to 0° C. and treated with a sodium borohydride pellet (0.12 g, 3.0 mmol) under an argon atmosphere. After stirring for 19 hr at room temperature, the reaction mixture was cooled to 0° C. and water was added cautiously until effervescence had ceased. The mixture was evaporated under reduced pressure and the residue neutralised with solid $K_2CO_3$. The product was extracted into EtOAc. The combined organic layers were dried ($Na_2SO_4$) and evaporated under reduced pressure to give the crude product. Purification by flash column chromatography using $CH_2Cl_2$ as eluant gave the title compound 0.11 g, 22%).

$^1$H NMR (250MHz, $CDCl_3$) δ: 7.52 (dd, 1H), 7.18 (d, 1H), 7.09 (d, 1H), 3.58 (t, 2H), 3.28 (t, 2H), 3.06 (t, 2H), 2.55 (t, 2H) 2.32 (s, 6H).

Description 4 6-Amino-2,3-dihydro-1-(2-dimethylaminoethyl)-1H-indole

Following the procedure outlined in description 2, reaction of the product from description 3 (0.1 g, 0.5 mmol) afforded the title compound as a brown oil (0.11 g, 100%)

$^1$H NMR (250MHz, $CDCl_3$) δ: 6.72 (d, 1H), 5.90 (d, 1H), 5.79 (s, 1H), 3.40 (brs, 2H) 3.28 (t, 2H), 3.03 (t, 2H), 2.78 (t, 2H), 2.43 ( t, 2H), 2.20 (s, 6H)

Description 5 4-(2-Dimethylaminoethyl)-6-nitro-2H-1,4-benzoxazin-3(4H)-one

To a suspension of 6-nitro-2H- 1,benzoxazin-3(4H)-one (J. Med. Chem. 1989, 32, 1627–1630) 1 g, 5.7 mmol) in dry THF (20 ml) at 0° C. under argon, was added NaH (0.16 g, 5.7 mmol 80% dispersion in mineral oil). A solution of 2-dimethylaminoethyl chloride (2.3 g, 20.8 mmol) in dry toluene (15 ml) was added and the reaction mixture heated under reflux for 19 hr. After cooling, water was added dropwise until effervescence had ceased, then the mixture was separated and the aqueous further extracted with EtOAc. The organic layers were combined, dried ($Na_2SO_4$) and evaporated under reduced pressure to give a pale brown solid (1.08g, 79%)

$^1$H NMR (250MHz, $CDCl_3$) δ: 8.03 (d, 1H), 7.94 (dd, 1H), 7.04 (d,1H), 4.73 (s,2H), 4.11 (t, 2H) 2.6 (t, 2H), 2.35 (s,6H).

Description 6 3,4-Dihydro-4-(2-dimethylaminoethyl)-6-nitro-2H-1,4-benzoxazine Boron trifluoride etherate (2 ml, 16.2 mmol) was added dropwise to a suspension of sodium borohydride (0.46 g, 12 mmol) in dry THF (30 ml) at 0° C., under argon. After 1 hr, a solution of the product from description 5 (1.08 g, 4 mmol) in dry TBF (20 ml) was added. The reaction mixture was heated under reflux for 2 hr, then cooled in ice. Aqueous $NaHCO_3$ was added dropwise until effervescence ceased, then the solvent was removed under reduced pressure and the residue dissolved in a mixture of EtOH (10 ml) and 5N HCl (10 ml) and heated under reflux for 45 minutes. After cooling, the solvent was removed under reduced pressure. The residue was treated with saturated $K_2CO_3$ solution to pH 8, then extracted with EtOAc. The combined extracts were dried ($Na_2SO_4$) and evaporated under reduced pressure to give the title compound (0.94 g, 92%).

$^1$H NMR (200MHz, $CDCl_3$) δ: 7.52 (m, 2H) 6.78 (d, 1H), 4.30 (t, 2H), 3.42 (m, 4H), 2.56 (t, 2H), 2.31 (s, 6H)

Description 7 6-Amino-3,4-dihydro-4-(2-dimethylaminoethyl)-2H-1,4-benzoxazine

Following the procedure outlined in description 2, reaction of the product from description 6 (0.94 g, 4 mmol) afforded the title compound as a brown oil (0.84 g, 100%).

$^1$H NMR (200MHz, $CDCl_3$) δ: 6.58 (d, 1H), 6.08 (d, 1H), 5.98 (dd, 1H), 4.13 (t, 2H), 3.35 (m, 6H), 2.50 (t, 2H), 2.30 (s, 6H).

Description 8 6-Amino-4-(2-dimethylaminoethyl)-2H-1,4-benzoxazin-3(4H)-one 4-(2-Dimethylaminoethyl)-6-nitro-2H-1,4-benzoxazin-3(4H)-one (D5) (0.175 g, 0.6 mmol) was hydrogenated in 1:1 ethanol/acetic acid (20 ml) for 5.5 h. Catalyst was removed by filtration through kieselguhr, and the filtrate was evaporated, dissolved in dichloromethane, washed with $K_2CO_3$ solution, dried ($Na_2SO_4$) and evaporated again to give the title compound (0.145 g, 93%) as a yellow-brown solid.

$^1$H NMR (200 MHz, $CDCl_3$) δ(ppm): 6.79 (d, 1H), 6.39 (d, 1H), 6.32 (dd, 1H), 4.50 (s, 2H), 3.99 (t, 2H), 3.61 (bs, 2H), 2.53 (t, 2H), 2.32 (s, 6H)

Description 9 3-Methyl-6-nitro-2H-1,4-benzoxazine

To a stirred solution of 2-amino-4-nitrophenol (1.0 g, 6.48 mmol) in acetone (250 ml) was added $K_2CO_3$ (1.35 g, 9.73 mmol). The reaction mixture was stirred at room temperature under Ar for 3 h. Chloroacetone (0.52 ml, 6.48 mmol) and $K_2CO_3$ (1.35 g, 9.73 mmol) were then added and the mixture was heated to reflux under Ar for 3 h, then allowed to cool and filtered through kieselguhr. The filtrate was concentrated in vacuo to afford the title compound as a dark red solid (1.25g, 100%)

$^1$H NMR (200 MHz, $CDCl_3$) δ(ppm): 8.15 (d, 1H), 8.02 (dd, 1H), 6.90 (d, 1H), 4.70 (s, 2H), 2.20 (s, 3H).

Description 10 3,4-Dihydro-3-methyl-6-nitro.2H-1,4-benzoxazine

3-Methyl-6-nitro-2H-1,4-benzoxazine (D9, 1.25 g, 6.47 mmol) in ethanol (30 ml) was treated portionwise over 10 minutes with sodium tetrahydroborate (0.88 g, 23.2 mmol). The reaction mixture was stirred at room temperature for 2 hours, then treated with water (60 ml) and dilute HCl (2 ml) and concentrated in vacuo. The residue was basified using saturated aqueous $K_2CO_3$ solution (60 ml) and extracted using ethyl acetate (3×100 ml). Combined organic extracts were dried ($Na_2SO_4$) and then concentrated in vacui to afford the title compound as a deep red crystalline solid (1.00 g, 80%).

$^1$H NMR (200 MHz, $CDCl_3$) δ(ppm): 7.58 (dd, 1H), 7.48 (d, 1H), 6.80 (d, 1H), 4.30 (m, 1H), 4.05 (b, 1H), 3.85 (dd, 1H), 3.55 (m, 1H), 1.25 (d, 3H).

Description 11 4-(2-Chloroacetyl)-3,4-dihydro-3-methyl-6-nitro-2H-1,4-benzoxazine A stirred solution of 3,4-dihydro-3-methyl-6-nitro-2H-1,4-benzoxazine (D10, 347 mg, 1.78 mmol) and triethylamine (0.50 ml, 3.55 mmol) in chloroform (10 ml) at 0° C. under Ar was treated with chloroacetyl chloride (0.28 ml, 3.55 mmol). The reaction mixture was stirred at room temperature for 2 hours, then treated with water (100 ml) and acidified using 5M HCl. The organic phase was extracted using chloroform (2×100 ml). Combined organic extracts were dried ($Na_2SO_4$) and concentrated in vacuo to afford the title compound as a brown oil (461 mg, 95%).

$^1$H NMR (200 MHz, $CDCl_3$) δ(ppm): 8.28 (b, 1H), 8.03 (dd, 1H), 7.05 (d, 1H), 4.75 (b, 1H), 4.30 (m, 4H), 1.30 (d, 3H).

Description 12 3,4-Dihydro-4-(2-dimethylaminoacetyl)-3-methyl-6-nitro-2H- 1,4-benzoxazine 4-(2-Chloroacetyl)-3,4-dihydro-3-methyl-6-nitro-2H-1,4-benzoxazine (D11, 461 mg, 1.70 mmol) in ethanol (20 ml) was treated with dimethylamine (4 ml of 5.6 M solution in ethanol). The suspension was left to stir at room temperature for 48 hours. The resulting mixture was concentrated in vacuo to afford the title compound as a brown solid (422 mg, 88%).

$^1$H NMR (200 MHz, $CDCl_3$) δ(ppm): 9.02 (s, 1H), 8.00 (dd, 1H), 7.00 (d, 1H), 5.00 (b, 1H), 4.29 (ABX, 2H), 3.45 (d, 1H), 3.19 (m, 1H), 2.38 (s, 6H), 1.29 (d, 3H).

Description 13 6-Amino-3,4-dihydro-4-(2-dimethylaminoacetyl)-3-methyl-2H-1,4-benzoxazine 3,4-Dihydro-4-(2-dimethylaminoacetyl)-3-methyl-6-nitro-2H-1,4-benzoxazine (D12, 422 mg, 1.51 mmol) was hydrogenated in ethanol (30 ml) over 10% palladium-charcoal (200 mg) at room temperature and atmospheric pressure for 18 hours. The catalyst was removed by filtration through kieselguhr, and the filtrate concentrated in vacuo to afford the title compound as a brown solid (304 mg, 80%). This was used without purification in the next step.

Description 14 6-Amino-3,4-dihydro-4-(2-dimethylaminoethyl)-3-methyl-2H-1,4-benzoxazine To a stirred suspension of lithium aluminium hydride (70 mg, 1.83 mmol) in dry tetrahydrofuran (TBF) (60 ml) at 0° C. under Ar was added dropwise, a solution of 6-amino-3,4-dihydro-4-(2-dimethylaminoacetyl)-3-methyl-2H-1,4-benzoxazine (D13, 304 mg, 1.22 mmol) in TBF (10 ml). The reaction mixture was heated under reflux for 2.5 hours, then allowed to cool to room temperature, after which it was treated with water (0.07 ml), 10% NaOH solution (0.07 ml) and water (0.21 ml). The mixture was filtered through kieselguhr and the filtrate dried ($Na_2SO_4$) and concentrated in vacuo to afford a yellow oil (160 mg). This was chromatographed on silica gel eluting with 5–40% MeOH/ $CH_2Cl_2$ to afford the title compound as a dark brown oil (61.7 mg, 22%).

$^1$H NMR (200 MHz, $CDCl_3$) δ(ppm): 6.60 (d, 1H), 6.03 (d, 1H), 5.95 (dd, 1H), 3.95 (m, 2H), 3.51-3.12 (m, 5H), 2.50 (t, 2H), 2.30 (s, 6H), 1.20 (d, 3H)

Description 15 Methyl (3,4-dihydro-2H-benzo[b]pyran-4-ylidene)acetate, E- and Z- isomers Sodium hydride (80% in mineral oil, 4.90 g, 0.16 mol) was stirred under Ar in dry TBF (200 ml) as trimethyl phosphonoacetate (26.2 ml, 0.16 mol) was added in dry TEF (50 ml) vmaintaining the temperature at ca 20° C., by standing in ice. 4-Chromanone (10.92 g, 0.07 mol) was added in dry TBF (100 ml), and the mixture was then stirred at ambient temperature for 3 days. The mixture was diluted with water (1000 ml), and extracted with dichloromethane. The extract was dried ($Na_2SO_4$) and evaporated to an orange oil, which was chromatographed on silica gel, eluting with 10% ethyl acetate in petroleum ether (b.p. 60°–80° C.). This gave pure E-isomer (4.55 g), pure Z-isomer (2.90 g), and a mixture of the two isomers (1.66 g) (total yield: 9.11 g, 60%).

E-isomer: $^1$H NMR (200 MHz, $CDCl_3$) δ(ppm): 7.61 (dd, 1H), 7.30 (m, 1H), 6.90 (m, 2H), 6.35 (s, 1H), 4.24 (t, 2H), 3.76 (s, 3H), 3.40 (td, 2H).

Z-isomer: $^1$H NMR (200 MHz, $CDCl_3$) δ(ppm): 7.79 (dd, 1H), 7.26 (td, 1H), 6.85 (m, 2H), 5.70 (s, 1H), 4.38 (t, 2H), 3.75 (s, 3H), 2.65 (td, 2H).

Description 16 Methyl (3,4-dihydro-2H-benzo[b]pyran-4-yl)acetate

A mixture of E- and Z-methyl (3,4-dihydro-2H-benzo[b]pyran-4-ylidene)acetate (D15) (5.14 g, 25 mmol) was hydrogenated over 10% palladium on charcoal (1.00 g) in ethanol (100 ml) for 2 h. Catalyst was filtered off onto kieselguhr, and the filtrate was evaporated to give the title compound (4.64 g, 89%) as a colourless oil.

$^1$H NMR (200 MHz, $CDCl_3$) δ(ppm): 7.1 (m, 2H), 6.85 (m, 2H), 4.2 (m, 2H), 3.73 (s, 3H), 3.36 (sextet, 1H), 2.82 and 2.55 (ABX, 2H), 2.17 (m, 1H), 1.86 (m, 1H).

Description 17 (3,4-Dihydro-2H-benzo[b]pyran-4-yl)acetic acid

Methyl (3,4-dihydro-2H-benzo[b]pyran4-yl)acetate (D16) (4.64 g, 22 mmol) was stirred in ethanol (50 ml) as sodium hydroxide (1.80 g, 45 mmol) was added in water (10 ml). The mixture was stirred for 1 h, concentrated in vacuo, diluted with water, and acidified with 5M HCl. The white solid, the title compound (3.69 g, 85%), was filtered off and dried.

$^1$H NMR (200 MHz, CDCl$_3$) δ(ppm): 7.13 (m, 2H), 6.86 (m, 2H), 4.21 (m, 2H), 3.38 (sextet, 1H), 2.89 and 2.60 (ABX, 2H), 2.20 (m, 1H), 1.92 (m, 1H).

Description 18 N,N-Dimethyl-(3,4-dihydro-2H-benzo[b]pyran-4-yl)acetamide (3,4-Dihydro-2H-benzo[b]pyran-4-yl)acetic acid (D17) (1.89 g, 9.8 mmol) was stirred at reflux under Ar in thionyl chloride (20 ml) for 45 min, cooled and evaporated to give a brown oil. This was dissolved in dichloromethane (30 ml), and dimethylamine (40% aqueous solution, 5 ml) was added. This mixture was stirred for 30 min, treated with dilute Na$_2$CO$_3$ solution (50 ml), and separated. The organic portion was dried (Na$_2$SO$_4$) and evaporated to give the title compound (2.22 g, 100%) as a brown oil.

$^1$H NMR (250 MHz, CDCl$_3$) δ(ppm): 7.11 (m, 2H), 6.85 (m, 2H), 4.19 (m, 2H), 3.48 (sextet, 1H), 3.00 (s, 3H), 2.96 (s, 3H), 2.77 and 2.56 (ABX, 2H), 2.22 (m, 1H), 1.87 (m, 1H).

Description 19 N,N-Dimethyl-(6-amino-3,4-dihydro-2H-benzo[b]pyran-4-yl) acetamide and N,N-dimethyl-(8-amino-3,4-dihydro-2H-benzo[b]pyran-4-yl)acetamide N,N-Dimethyl-(3,4-dihydro-2H-benzo[b]pyran-4-yl) acetamide (D18) (0.84 g, 3.8 mmol) was stirred in acetic anhydride (10 ml) as copper (II) nitrate trihydrate (1.23 g, 5.1 mmol) was added, cooling the mixture by standing in a cold water bath. The mixture was stirred for 1h, poured into K$_2$CO$_3$ solution, and extracted with dichloromethane. The extract was dried (Na$_2$SO$_4$) and evaporated, giving a mixture of the intermediate nitro compounds (1.04 g). This was hydrogenated over 10% palladium on charcoal (0.50 g) in ethanol (25 ml)/acetic acid (10 ml) for 6 h. Catalyst was filtered off onto kieselguhr, and the filtrate was concentrated, diluted with dichloromethane, washed with NaHCO$_3$ solution, dried (Na$_2$SO$_4$) and evaporated to give a dark oil (0.50 g). Chromatography on silica gel, eluting with 0–4% methanol in dichloromethane gave the 8-amino compound (0.177 g, 19%), followed by the 6-amino compound (0.091 g, 10%), both as light brown gums.

8-Amino isomer: $^1$H NMR (200 MHz, CDCl$_3$) δ(ppm): 6.71 (d, 1H), 6.55 (m, 2H), 4.24 (m, 2H), 3.7 (b, 2H), 3.43 (sextet, 1H), 2.98 (s, 3H), 2.96 (s, 3H), 2.77 and 2.53 (ABX, 2H), 2.21 (m, 1H), 1.85 (m, 1H).

6-Amino isomer: $^1$H NMR (200 MHz, CDCl$_3$) δ(ppm): 7.63 (d, 1H), 6.50 (m, 2H), 4.11 (m, 2H), 3.5 (b, 2H), 3.39 (sextet, 1H), 2.99 (s, 3H), 2.96 (s, 3H), 2.72 ad 2.53 (ABX, 2H), 2.17 (m, 1H), 1.78 (m, 1H).

Description 20 2-(6-Amino-3,4-dihydro-2H-benzo[b]pyran-4-yl)-N,N-dimethylethylamine N,N-Dimethyl-(6-amino-3,4-dihydro-2H-benzo[b]pyran-4-yl)acetamide (D19) (0.019 g, 0.39 mmol) was added in dry IHP (8 ml) to a suspension of lithium aluminium hydride (0.030 g, 0.79 mmol) in dry TBF (2 ml). The mixture was stirred at reflux under Ar for 3h, cooled and treated successively with water (0.03 ml), 10% NaOH (0.03 ml) and water (0.09 ml). It was then diluted with ethyl acetate, dried (Na$_2$SO$_4$) and filtered. Evaporation then gave the title compound (0.068 g, 79%) as a brown gum.

$^1$H NMR (200 MHz, CDCl$_3$) δ(ppm): 6.62 (d, 1H), 6.50 (m, 2H), 4.10 (m, 2H), 3.35 (b, 2H), 2.80 (sextet, 1H), 2.36 (m, 2H), 2.25 (s, 6H), 2.02 (m, 2H), 1.72 (m, 2H)

Description 21 5-Nitro-2(3H)-benzoxazolone

A stirred solution of 2-amino--nitrophenol (1.50 g, 9.7 mmol) and 1,1'-carbonyldiimidazole (1.74 g, 10.7 mmol) in N,N-dimethylformamide (20 ml) was heated at 80° C. under Ar for 2 hours. The cooled reaction mixture was then poured into water (300 ml) and the resulting solid was filtered off and dried, affording the title compound as a beige powder (1.22 g, 69%).

$^1$H NMR (200 MHz, d$^6$DMSO) δ(ppm): 8.06 (dd, 1H), 7.85 (d, 1H), 7.53 (d, 1H), 3.50 (b, 1H)

Description 22 3-(2-Dimethylaminoethyl)-5-nitro-2(3H)-benzoxazolone

To a stirred solution of 2-dimethylaminoethyl chloride hydrochloride (4.88 g, 34 mmol) in water (50 ml) was added solid anhydrous K$_2$CO$_3$ until completely saturated. This suspension was then extracted with toluene (2×50 ml). The combined extract was dried (Na$_2$SO$_4$) and the resulting solution added dropwise to a stirred suspension of 5-nitro-2(3H)-benzoxazolone (1)21) (1.22 g, 6.8 mmol) and sodium hydride (0.22 g, 7.45 mmol) in tetrahydrofuran (100 ml) at 0° C. under Ar. The reaction mixture was heated under reflux for 3 hours. Cold water was run into the cooled mixture until effervesence had ceased, then the mixture was acidified using 5M HCl and washed with ethyl acetate (2×100 ml). The aqueous solution was basified using saturated K$_2$CO$_3$ solution and then extracted using ethyl acetate (2×100 ml). The combined organic extracts were dried (Na$_2$SO$_4$) and concentrated in vacuo to afford the title compound as a yellow solid (0.47 g, 27%).

$^1$H NMR (200 MHz, CDCl$_3$/d$^6$DMSO) δ(ppm): 8.12 (dd, 1H), 7.98 (d, 1H), 7.38 (d, 1H), 4.00 (t, 2H), 2.70 (t, 2H), 2.30 (s, 6H)

Description 23 5-Amino-3-(2-dimethylaminoethyl)-2(3H)-benzoxazolone

A solution of 3-(2-dimethylaminoethyl)-5-nitro-2(3H)-benzoxazolone (D22) (0.47 g, 187 mmol) in ethanol (60 ml) was hydrogenated over 10% palladium-charcoal (0.2 g) at atmospheric pressure and temperature for 18 hours. The catalyst was removed by filtration through kieselguhr and the filtrate concentrated in vacuo to afford the title compound as a green oil (0.36 g, 88%).

$^1$H NMR (200 MHz, CDCl$_3$) δ(ppm): 6.95 (d, 1H), 6.41 (d, 1H), 6.35 (s, 1H), 3.85 (t, 2H), 3.70 (b, 2H), 2.62 (t, 2H), 2.31 (s, 6H)

Description 24 7-Nitro-2,3,4,5-tetrahydro-1,5-benzoxazepine 2,3,4,5-Tetrahydro-1,5-benzoxazepine (Zh. Obshch. Khim. 1963, 33, 322) (340 mg, 2.27 mmol) was treated with 5M sulphuric acid (0.5 ml) and ethanol (10 ml). This solution was stirred for five minutes and then concentrated in vacuo to afford a brown oil, which was dissolved in concentrated sulphuric acid (10 ml) and cooled to 10° C. under Ar. This solution was treated with potassium nitrate (0.29 g, 2.84 mmol) over 20 minutes maintaining the temperature between 15°–18° C. The reaction mixture was then stirred at room temperature for 1.5 hours, after which it was added to an ice/water mixture (~100 ml). This solution was basified using 40% sodium hydroxide solution, and then extracted using ethyl acetate. The combined organic extracts were dried (Na$_2$SO$_4$) and concentrated in vacuo to afford a yellow/brown solid. This was chromatographed on silica gel eluting with ethyl acetate to afford the tide compound as an orange solid (174.6 mg, 39%).

$^1$H NMR (200 MHz, CDCl$_3$) δ(ppm): 7.61 (m, 2H), 6.95 (d, 1H), 4.25 (t, 2H), 3.96 (b, 1H), 3.35 (m, 2H), 2.10 (m, 2H)

Description 25 7-Amino-5-(2-dimethylaminoethyl)-2,3,4,5-tetrahydro-1,5-benzoxazepine The title compound was prepared from 7-nitro-2,3,4,5-tetrahydro-1,5-benzoxazepine (D24) as a brown oil (132 mg, 82%) using the methodology of Descriptions 11,12,13 and 14.

¹H NMR (200 MHz, CDCl₃) δ(ppm): 6.75 (m, 1H), 6.13 (m, 2H), 4.00 (m, 2H), 3.20 (m, 6H), 2.55 (t, 2H), 2.30 (s, 6H), 1.95 (t, 2H)

Example 1 N-[1-(2-Dimethylaminoethyl)-1H-indol-6-yl]-2'-methyl-4'-(5-methyl-1,2,4-oxadiazol-3-yl)biphenyl-4-carboxamide 2'-Methyl-4'-(5-methyl-1,2,4-oxadiazol-3-yl)biphenyl-4-carboxylic acid (E.P.0533268-A1) (0.19 g, 0.7 mmol) was suspended in CH₂Cl₂ (15 ml) and treated with oxalylchloride (0.065 ml, 0.074 mmol) followed by a drop of DMF. The mixture was stirred at room temperature for 1 hr, then evaporated under reduced pressure to give a pale yellow solid.

The solid was redissolved in dichloromethane (10 ml) and added to a solution of the product from decsription 2 (0.14 g, 0.7 mmol) in CH₂Cl₂ (10 ml) containing Et₃N (0.19 ml, 1.4 mmol) under argon. After 19 hr at room temperature, the reaction mixture was treated with water (20 ml),extracted with CH₂Cl₂ and the combined organic layers were dried (Na₂SO₄) and evaporated under reduced pressure to give a brown oil which was purified by flash column chromatography using CH₂Cl₂ as eluant. The title compound was isolated as a white solid. (90 mg, 30%)

¹H NMR (250mHz, CDCl₃) δ: 8.40 (s, 1H) 8.20 (s, 1H) 7.99-7.90 (m, 4H), 7.53 (d, 1H), 7.39 (d, 2H), 7.30 (d, 1H), 7.12 (d, 1H), 7.08 (dd, 1H), 6.46 (d, 1H), 4.18 (t, 2H), 2.71-2.65 (m, 5H), 2.31 (s, 3H), 2.25 (s, 6H).

Example 2 N-[2,3-Dihydro-1-(2-dimethylaminoethyl)-1H-indol-6-yl]-2'-methyl-4'-(5-methyl-1,2,4-oxadiazol-3-yl)biphenyl-4-carboxamide Following the procedure outlined in Example 1, reaction of the product from description 4 (0.11 1g, 0.5 mmol) afforded the title compound as a white solid (90 mg, 48%)

¹H NMR (250MHz, CDCl₃) d: 8.01 (s, 1H), 7.99-7.92 (m, 3H), 7.80 (s, 1H), 7.48 (d, 2H), 7.38 (d, 1H), 7.03 (m, 2H), 6.79 (dd, 1H), 3.48 (t, 2H), 3.30 (t, 2H), 2.98 (t,2H), 2.69 (s, 3H), 2.64 (t, 2H), 2.38 (s,6H) 2.35 (s, 3H).

Example 3 N-[4-(2-Dimethylaminoethyl)-3,4-dihydro-2H-1,4-benzoxazin-6-yl]-2'-methyl-4'-(5-methyl-1,2,4-oxadiazol-3-yl)biphenyl-4-carboxamide Following the procedure outlined in Example 1 reaction of the product from description 7 (0.16 g, 0.7 mmol) afforded the title compound as a pale yellow solid (0.11 g, 39%).

¹H NMR (250MHz, CDCl₃) δ: 8.02 (s, 1H), 7.98 (m, 3H), 7.78 (s, 1H), 7.48 (d, 2H), 7.35 (d, 1H), 7.22 (s, 1H), 6.77 (s, 2H), 4.23 (t, 2H), 3.45 (m, 4H), 2.70 (s, 3H), 2.59(t, 2H), 2.35 (s, 3H), 2.31 (s, 6H)

Example 4 N-[3-(2-Dimethylaminoethyl)-1H-indol-5-yl]-2'-methyl-4'-(5-methyl-1,2,4-oxadiazol-3-yl)biphenyl-4-carboxamide The title compound was prepared from 5-amino-3-(2-dimethylaminoethyl)-1H-indole (J. E. acor, Syn Comm. 1993, 23, 65) using the procedure of Example 1.

¹H NMR (250 MHz, CDCl₃) δ(ppm): 8.65 (s, 1H), 8.25 (s, 1H), 8.00-7.85 (m, 6H), 7.45 (d, 2H), 7.35-7.30 (m, 2H), 6.95 (s, 1H), 2.90 (t, 2H), 2.70-2.50 (m, 8H), 2.30 (s, 6H).

Example 5 N-[4-(2-Dimethylaminoethyl)-3,4-dihydro-3-oxo-2H-1,4-benzoxazin-6-yl]-2'-methyl-4'-(5-methyl-1,2,4-oxadiazol-3-yl)biphenyl-4-carboxamide 2'-Methyl-4'-(5-methyl-1,2,4-oxadiazol-3-yl)biphenyl-4-carboxylic acid (EP 0553268A1) (0.188 g, 0.64 mmol) was converted to the acyl chloride by stirring at reflux under Ar in thionyl chloride (10 ml) for 45 min, cooling, and then evaporating to dryness. This was reacted with 6-amino-4-(2-dimethylaminoethyl)-1,4-benzoxazin-3(4H)-one (D8) (0.150 g, 0.64 mmol) following the procedure of Example 1. This gave the title compound (0.247 g, 75%) as a white foam, which was converted to the oxalate, a white solid.

¹H NMR (oxalate, 250 MHz, d₆-DMSO) δ(ppm): 10.40 (s, 1H), 8.09 (d, 2H), 8.00 (s, 1H), 7.94 (d, 1H), 7.72 (d, 1H), 7.58 (d, 2H), 7.52 (dd, 1H), 7.46 (d, 1H), 7.05 (d, 1H), 4.68 (s, 2H), 4.23 (t, 2H), 3.23 (t, 2H), 2.80 (s, 6H), 2.69 (s, 3H), 2.28 (s, 3H)

m.s. (m/z) M⁺511. C₂₉H₂₉N₅O₄ requires M⁺511

Example 6 N-[4-(2-Dimethylaminoethyl)-3,4-dihydro-3-methyl-2H-1,4-benzoxazin-6-yl]-2'-methyl-4'-(5-methyl-1,2,4-oxadiazol-3-yl)biphenyl-4-carboxamide 2'-Methyl-4'-(5-methyl-1,2,4-oxadiazol-3-yl)biphenyl-4-carboxylic acid (EP 0533268A1) (77 mg, 0.26 mmol) was treated with thionyl chloride (5 ml) and the mixture heated under reflux under Ar for 1 hour, then concentrated in vacuo to afford a yellow solid. This was dissolved in dichloromethane (5 ml) and treated with a solution of 6-amino-3,4-dihydro-4-(2-dimethylaminoethyl)-3-methyl-2H-1,4-benzoxazine (D14, 61.7 mg, 0.26 mmol) and triethylamine (0.11 ml, 0.78 inmol) in dichloromethane (10 ml). The reaction mixture was stirred at room temperature under Ar for 24 hours, then washed with brine/saturated potassium carbonate solution (30 ml of a 1:1 solution). The organic layer was separated, dried (Na₂SO₄) and concentrated in vacuo to afford a brown oil. This was chromatographed on SiO₂, eluting with 0–8% methanol/dichloromethane to afford the title compound as a light yellow oil (72.2 mg, 54%).

¹H NMR (200 MHz, CDCl₃) δ(ppm): 7.95 (m, 4H), 7.81 (s, 1H), 7.45 (d, 2H), 7.34 (d, 1H), 7.18 (s, 1H), 6.78 (m, 2H), 4.01 (m, 2H), 3.60-3.25 (m, 3H), 2.70 (s, 3H), 2.58 (t, 2H), 2.35 (s, 9H), 1.25 (d, 3H).

Example 7 N-[4-(2-Dimethylaminoethyl)-3,4-dihydro-2H-benzo[b]pyran-6-yl]-2'-methyl-4'-(5-methyl-1,2,4-oxadiazol-3-yl)biphenyl-4-carboxamide The title compound was prepared from 2-(6-amino-3,4-dihydro-2H-benzo[b]pyran-4-yl)-N,N-dimethylethylamine (D20) (0.068 g, 0.31 mmol), following the procedure of Example 1, as a yellow-brown gum, in 36% yield. This was converted to the oxalate, a buff solid.

¹H NMR (oxalate, 200 MHz, d₆-DMSO) δ(ppm): 10.24 (s, 1H), 8.1-7.9 (m, 4H), 7.72 (m, 1H), 7.58 (d, 2H), 7.47 (d, 2H), 6.77 (d, 1H), 4.15 (m, 2H), 3.14 (t, 2H), 2.91 (m, 1H), 2.76 (s, 6H), 2.70 (s, 3H), 2.37 (s, 3H), 2.2-1.75 (m, 4H)

M.S. (m.z) M⁺496. C₃₀H₃₂N₄O₃ requires M⁺496

Example 8 N-[3-(2-Dimethylaminoethyl)-2-oxo-2(3H)-benzoxazol-5-yl]-2'-methyl-4'-(5-methyl-1,2,4-oxadiazol-3-yl)biphenyl-4-carboxamide 2'-Methyl-4'-(5-methyl-1,2,4-oxadiazol-3-yl)biphenyl-4-carboxylic acid (EP 0553268 A1) (245 mg, 0.83 mmol) was stirred in thionyl chloride (5 ml) at gentle reflux under Ar for 1 hour and then concentrated in vacuo to dryness. The solid was dissolved in dichloromethane (5 ml) and added to a stirred solution of 5-amino-3-(2-dimethylaminoethyl)-2(3H)-benzoxazolone (D23) (183.5 mg, 0.83 mmol) in dichloromethane (5 ml) containing triethylamine (0.24 ml, 2.5 mmol). The reaction mixture was stirred at room temperature under Ar for 48 hours, then washed with saturated potassium carbonate solution/brine (100 ml of 1:1 solution). The organic layer was dried (Na₂SO₄) and concentrated in vacuo affording an off-white solid. This was chromatographed on silica gel eluting with 5% methanoldichloromethane affording the title compound as a white solid (225 mg, 55%).

¹h NMR (200 MHz, CDCl₃) δ(ppm): 8.15 (s, 1H), 7.95 (m, 6H), 7.50 (d, 1H), 7.41 (d, 1H), 7.15 (d, 1H), 7.00 (dd, 1H), 3.95 (t, 2H), 2.70 (s+t, 5H), 2.35 (s, 3H), 2.29 (s, 6H)

Example 9 N-[5-(2-Dimethylaminoethyl)-2,3,4,5-tetrahydro-1,5-benzoxazepin-7-yl]-2'-methyl-4'-(5-methyl-1,2,4-oxadiazol-3-yl)biphenyl-4-carboxamide The title compound was prepared from 7-amino-5-(2-dimethylaminoethyl)-2,3,4,5-tetrahydro-1,5-benzoxazepine (d25) as a brown oil (56 mg, 20%) using the method of Example 6.

$^1$H NMR (200 MHz, CDCl$_3$) δ(ppm): 8.10 (s, 1H), 7.96 (m, 5H), 7.44 (d, 1H), 7.30 (m, 3H), 6.90 (d, 1H), 4.12 (t, 2H), 3.40 (m, 4H), 2.70 (t, 5H), 2.40 (s, 6H), 2.32 (s, 3H), 2.02 (t, 2H)

We claim:

1. A compound of formula (I) or a salt thereof:

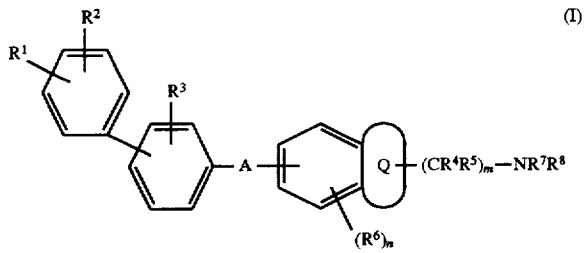

in which A is CONR where R is hydrogen or C$_{1-6}$alkyl; Q is an optionally substituted 5 to 7-membered heterocyclic ring containing 1 to 3 heteroatoms selected from oxygen, nitrogen or sulphur, R$^1$ is hydrogen, halogen, C$_{1-6}$alkyl, C$_{3-6}$cycloalkyl, COC$_{1-6}$alkyl, C$_{1-6}$alkoxy, hydroxy, hydroxyC$_{1-6}$alkyl, hydroxyC$_{1-6}$alkoxy, C$_{1-6}$alkoxyC$_{1-6}$alkoxy, acyl, nitro, trifluoromethyl, cyano, SR$^9$, SOR$^9$, SO$_2$R$^9$, SO$_2$NR$^{10}$R$^{11}$, CO$_2$R$^{10}$, CONR$^{10}$R$^{11}$, CO$_2$NR$^{10}$R$^{11}$, CONR$^{10}$(CH$_2$)$_a$CO$_2$R$^{11}$, (CH$_2$)$_a$NR$^{10}$R$^{11}$, (CH$_2$)$_a$CONR$^{10}$R$^{11}$, (CH$_2$)$_a$NR$^{10}$COR$^{11}$, (CH$_2$)$_a$CO$_2$C$_{1-6}$alkyl, CO$_2$(CH$_2$)$_a$OR$^{10}$, NR$^{10}$OR$^{11}$, NR$^{10}$CO$_2$R$^{11}$, NR$^{10}$CONR$^{10}$R$^{11}$, CR$^{10}$=NOR$^{11}$, CNR$^{10}$=NOR$^{11}$, where R$^{10}$ and R$^{11}$, are independently hydrogen or C$_{1-6}$alkyl and a is 1 to 4 or R$^1$ is an optionally substituted 5 to 7-membered heterocyclic ring containing 1 to 3 heteroatoms selected from oxygen, nitrogen or sulphur, R$^2$ and R$^3$ are independently hydrogen, halogen, C$_{1-6}$alkyl, C$_{3-6}$cycloalkyl, C$_{3-6}$cycloalkenyl, C$_{1-6}$alkoxy, acyl, aryl, acyloxy, hydroxy, nitro, trifluoromethyl, cyano, CO$_2$R$^{10}$, CONR$^{10}$R$^{11}$, NR$^{10}$R$^{11}$ where R$^{10}$ and R$^{11}$ are as defined for R$^1$; R$^4$ and R$^5$ are independently hydrogen or C$_{1-6}$alkyl; R$^6$ is halogen, hydroxy, C$_{1-6}$alkyl or C$_{1-6}$alkoxy; R$^7$ and R$^8$ are independently hydrogen, C$_{1-6}$alkyl, aralkyl, or together with the nitrogen atom to which they are attached form an optionally substituted 5- to 7-membered heterocyclic ring containing one or two heteroatoms selected from oxygen, nitrogen or sulphur, m is 0 to 4; and n is 0, 1 or 2.

2. A compound according to claim 1 in which R$^1$ is oxadiazole.

3. A compound according to claim 1 in which R$^2$ is C$_{1-6}$alkyl.

4. A compound according to claim 1 in which R$^3$ is hydrogen.

5. A compound according to claim 1 in which R$^4$ and R$^5$ are both hydrogen and m is 2.

6. A compound according to claim 1 in which n is 0.

7. A compound according to claim 1 which is:
N-[1-(2-Dimethylaminoethyl)-1H-indol-6-yl]-2'-methyl-4'-(5-methyl-1,2,4-oxadiazol-3-yl)biphenyl-4-carboxamide,
N-[2,3-Dihydro-1-(2-dimethylaminoethyl)-1H-indol-6-yl]-2'-methyl-4'-(5-methyl-1,2,4-oxadiazol-3-yl) biphenyl-4-carboxamide, N-[4-(2-Dimethylaminoethyl)-3,4-dihydro-2H-1,4-benzoxazin-6-yl]-2'-methyl-4'-(5-methyl-1,2,4-oxadiazol-3-yl)biphenyl-4-carboxamide, N-[3-(2-Dimethylaminoethyl)-1H-indol-5-yl]-2'-methyl-4'-(5-methyl-1,2,4-oxadiazol-3-yl)biphenyl-4-carboxamide, N-[4-(2-Dimethylaminoethyl)-3,4-dihydro-3-oxo-2H-1,4-benzoxazin-6-yl]-2'-methyl-4'-(5-methyl-1,2,4-oxadiazol-3-yl)biphenyl-4-carboxamide, N-[4-(2-Dimethylaminoethyl)-3,4-dihydro-3-methyl-2H-1,4-benzoxazin-6-yl]-2'-methyl-4'-(5-methyl-1,2,4-oxadiazol-3-yl)biphenyl-4-carboxamide, N-[4-(2-Dimethylaminoethyl)-3,4-dihydro-2H-benzo[b]pyran-6-yl]-2'-methyl4'-(5-methyl-1,2,4-oxadiazol-3-yl)biphenyl-4-carboxamide, N-[3-(2-Dimethylaminoethyl)-2-oxo-2(3H)-benzoxazol-5-yl]-2'-methyl-4'-(5-methyl-1,2,4-oxadiazol-3-yl)biphenyl-4-carboxamide, N-[5-(2-Dimethylaminoethyl)-2,3,4,5-tetrahydro-1,5-benzoxazepin-7-yl]-2'-methyl-4'-(5-methyl-1,2,4-oxadiazol-3-yl) biphenyl-4-carboxamide, and pharmaceutically acceptable salts thereof.

8. A pharmaceutical composition which comprises a compound according to claim 1 and a pharmaceutically acceptable carrier or excipient.

9. A method of treating depression by administering to a human in need thereof an effective amount of a compound of claim 1.

10. A process for the preparation of a compound of formula (I) according to claim 1 which comprises (a) reacting a compound of formula (II):

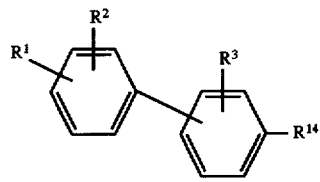

wherein R$^1$, R$^2$, R$^3$ and R$^4$ are as defined below, in a solvent with a base and a compound of formula (III):

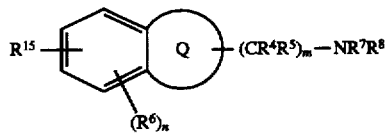

wherein Q, m, n, R$^1$, R$^2$, R$^3$, R$^4$, R$^5$, R$^6$, R$^7$ and R$^8$ are as defined in formula (I); R$^{14}$ is an acyl halide or an acid anhydride and R$^{15}$ is an amine group; and thereafter optionally converting the compound of formula (I), as defined in claim 1, into another compound of formula (I) and thereafter optionally forming a pharmaceutically acceptable salt.

* * * * *